(12) United States Patent
Oneda et al.

(10) Patent No.: US 9,744,696 B2
(45) Date of Patent: Aug. 29, 2017

(54) METHOD OF PRODUCING SOLID MATERIAL AND COMPRESSION MOLDING MACHINE

(71) Applicant: KIKUSUI SEISAKUSHO LTD., Kyoto-shi (JP)

(72) Inventors: Yoshitsugu Oneda, Kyoto (JP); Kunihiko Tsutsui, Kyoto (JP); Takao Terai, Koka (JP); Dai Ukai, Koka (JP); Toshiya Taniguchi, Koka (JP)

(73) Assignee: KIKUSUI SEISAKUSHO LTD., Kyoto-Shi, Kyoto (JP)

( * ) Notice: Subject to any disclaimer, the term of this patent is extended or adjusted under 35 U.S.C. 154(b) by 577 days.

(21) Appl. No.: 13/952,520

(22) Filed: Jul. 26, 2013

(65) Prior Publication Data
US 2014/0035203 A1 Feb. 6, 2014

(30) Foreign Application Priority Data

Aug. 3, 2012 (JP) ................. P2012-172694
Aug. 24, 2012 (JP) ................. 2012-185744

(51) Int. Cl.
*B29C 41/22* (2006.01)
*B30B 11/02* (2006.01)
*B30B 11/08* (2006.01)
*B30B 11/34* (2006.01)
*A61K 9/00* (2006.01)
*A61K 9/20* (2006.01)
*B29C 43/02* (2006.01)
*B29C 43/20* (2006.01)

(52) U.S. Cl.
CPC ............ *B29C 41/22* (2013.01); *A61K 9/0056* (2013.01); *A61K 9/2013* (2013.01); *A61K 9/2072* (2013.01); *A61K 9/2095* (2013.01); *B29C 43/02* (2013.01); *B29C 43/20* (2013.01); *B30B 11/027* (2013.01); *B30B 11/08* (2013.01); *B30B 11/34* (2013.01)

(58) Field of Classification Search
CPC ...................................... B29C 41/22
See application file for complete search history.

(56) References Cited

FOREIGN PATENT DOCUMENTS

| | | |
|---|---|---|
| JP | 2008-126309 A | 6/2008 |
| JP | 2012-035289 A | 2/2012 |
| WO | WO 2006/126561 A1 | 11/2006 |

*Primary Examiner* — Larry Thrower
(74) *Attorney, Agent, or Firm* — McGinn IP Law Group, PLLC.

(57) ABSTRACT

The invention provides a method of producing a solid material, and the method includes: applying a light coloring substance to at least one of an inner surface of a die bore, an upper end surface of a lower punch, and a lower end surface of an upper punch; filling a powdery material in the die bore; compression molding the powdery material filled in the die bore with use of the upper punch and the lower punch; and irradiating with light a molded product obtained by the compression molding to color the molded product.

19 Claims, 10 Drawing Sheets

METHOD OF PRODUCING SOLID MATERIAL AND COMPRESSION MOLDING MACHINE

BACKGROUND

Highly distinguishable tables and the like are demanded in medical practice in order to prevent erroneous preparation or administration of solid dosages such as tables.

There is a typical method for enhancing distinguishability by processing by engraving a tabletting tip surface to provide a letter or the like on a surface of a tablet. Such a tablet is, however, likely to have breakage at the engraved portion. Accordingly, there is developed a method of printing a letter or the like on a surface of a tablet with use of ink. Nevertheless, direct printing is not applicable to an uncoated tablet. Printing with use of ink causes defects such as variation in tone, bleeding, adhesion of undried ink to another tablet, and a blurred letter.

In order to solve these problems, WO2006/126561 discloses a method of marking a letter or a symbol by irradiating with constant laser light a surface of a tablet or the like including a composition for oral administration with change in color-inducing oxide (titanium oxide, yellow ferric oxide, or red ferric oxide) dispersed therein to aggregate particles of the change in color-inducing oxide so as to cause change in color.

Mixing change in color-inducing oxide in a composition for oral administration causes entire dispersion of the change in color-inducing oxide also inside the tablet or the like. This indicates that the tablet or the like contains a large amount of change in color-inducing oxide that is unnecessary for efficacy and effect of medicine.

Change in color-inducing oxide is desirably dispersed on a surface of a composition for oral administration. As a typical example, a tablet is produced by a compression molding machine and is then fed in a spray coater or a pan coater to be coated.

A tablet manufacturer needs to have a plurality of machines in a plant, including a spray coater or a pan coater. There is required the step of feeding tablets discharged from a compression molding machine into the spray coater or the pan coater. This causes necessity for a placement space as well as increase of production steps and a production period.

An orally disintegrating tablet is preferably produced through fewer steps because it is likely to chip more easily than an ordinary tablet.

Moreover, an orally disintegrating tablet being coated may deteriorate in collapsibility. Such deterioration in collapsibility occurs to a tablet having sugar coating as well as to a tablet having film coating.

JP 2012-35289 A discloses a method of producing a coated product with use of a compression molding machine, the method including the steps of: spraying to apply lubricant to an upper punch, a lower punch, and an inner surface of a die bore; spraying to apply a coating agent thereonto; filling a powdery material in the die bore; and compressing the powdery material with use of the upper punch and the lower punch. This production method achieves coating on an orally disintegrating tablet with no use of any additional machine such as a spray coater or a pan coater. There is thus caused no problem such as necessity for a placement space or increase of production steps.

JP 2012-35289 A, however, neither discloses nor suggests spraying a light coloring substance such as titanium oxide in the process of obtaining a molded product with use of the compression molding machine. There is no disclosure or suggestion of coloring the molded product by applying light.

SUMMARY OF THE INVENTION

The invention relates to a method of producing a solid material that has a mark such as a letter displayed by irradiating a molded product of a compression molding machine with light. It is an object of the invention to achieve reduction of a placement space, production steps, a production period, and a light coloring substance, as well as retention of preferred collapsibility.

The invention provides a method of producing a solid material with use of a compression molding machine including an upper punch, a lower punch, and a die bore formed in a table, the method including: applying a light coloring substance to at least one of an inner surface of the die bore, an upper end surface of the lower punch, and a lower end surface of the upper punch; filling a powdery material in the die bore; compression molding the powdery material filled in the die bore with use of the upper punch and the lower punch; and irradiating with light a molded product obtained by the compression molding to color the molded product.

In this method, the light coloring substance, which is applied to at least one of the inner surface of the die bore, the upper end surface of the lower punch, and the lower end surface of the upper punch, is deposited on a surface of the molded product by compression molding. There is thus obtained a desired solid material without need for any additional step such as coating to apply a light coloring substance after compression molding, or without use of a spray coater or a pan coater. It is possible to produce a solid material having a mark such as a letter colored with use of a small amount of a light coloring substance. Such a small amount of the applied light coloring substance hardly affects collapsibility of the molded product. Examples of the light coloring substance include oxide.

Preferably, the method further includes spraying outer lubricant to the inner surface of the die bore, the upper end surface of the lower punch, and the lower end surface of the upper punch.

The outer lubricant may be sprayed before or after application of the light coloring substance. The outer lubricant is preferably sprayed before the application in order for easier discharge from a mold tool. This production method further including spraying outer lubricant is applicable to production of an orally disintegrating tablet or the like.

In order to apply a light coloring substance more efficiently, there is exemplified a method of producing a solid material with use of a compression molding machine including an upper punch, a lower punch, and a die bore formed in a table, the method including: spraying a light coloring substance and outer lubricant to an inner surface of the die bore, an upper end surface of the lower punch, and a lower end surface of the upper punch; compression molding a powdery material filled in the die bore with use of the upper punch and the lower punch; and irradiating with light a molded product obtained by the compression molding to color the molded product.

The light coloring substance such as titanium oxide, red ferric oxide, and yellow ferric oxide easily aggregate to cause stuck before the spraying step. Such stuck of the light coloring substance is prevented by spraying a mixture of the outer lubricant and the light coloring substance. There is also no need to separately spray the outer lubricant because the outer lubricant is sprayed together. Appropriately mixing the outer lubricant and the light coloring substance at appropriate ratio exerts both of collapsibility and the light coloring property preferable for the molded product.

Examples of the light coloring substance according to the invention include a light coloring substance that is colored by irradiation with light as well as a light coloring substance that causes an adjacent powdery material or another material to be colored upon irradiation of the light coloring substance with light. The light coloring substance is desirably colored in the coloring step so as to achieve highly distinguishable coloring.

In order to color the light coloring substance, the light is preferably ultraviolet laser light.

In order to achieve highly distinguishable coloring, the light coloring substance can include at least one of titanium oxide, red ferric oxide, and yellow ferric oxide. Titanium oxide, red ferric oxide, or yellow ferric oxide is colored by application of ultraviolet laser light. The solid material thus has a letter or the like thereon. Titanium oxide includes titanium dioxide.

The solid material is preferably a solid dosage, in particular, an orally disintegrating tablet.

A compression molding machine according to the invention includes: a table having a die bore penetrating vertically; a lower punch located below the die bore and having an upper end to be inserted in the die bore so as to be slidable in the die bore, and an upper punch located above the die bore so as to face the lower punch and having a lower end to be inserted in the die bore so as to be slidable in the die bore; spraying device for spraying a light coloring substance and outer lubricant to an inner surface of the die bore, an upper end surface of the lower punch, and a lower end surface of the upper punch; filling device for filling in the die bore a powdery material to be compression molded by the upper punch and the lower punch after the spraying device sprays; and coloring device for irradiating with light a molded product obtained by the compression molding to color the molded product.

The powdery material in the invention refers to an aggregate of minute solids and includes an aggregate of particles such as what they call granules and an aggregate of powder smaller than the particles.

BRIEF DESCRIPTION OF THE DRAWINGS

FIGS. 6(I) to 6(IV) are views showing the steps of tabletting a molded product performed by the compression molding machine according to the embodiment;

DESCRIPTION OF THE PREFERRED EMBODIMENTS

Described below are embodiments of the present invention with reference to FIGS. 1 to 10.

First Embodiment

A compression molding machine according to the first embodiment is of a rotary type, for producing a molded product that includes an inner core obtained by compressing a powdery material and coating with a coating agent. If the molded product is a tablet, the powdery material is including an active ingredient, or including an active compound and an excipient.

Figure 1:
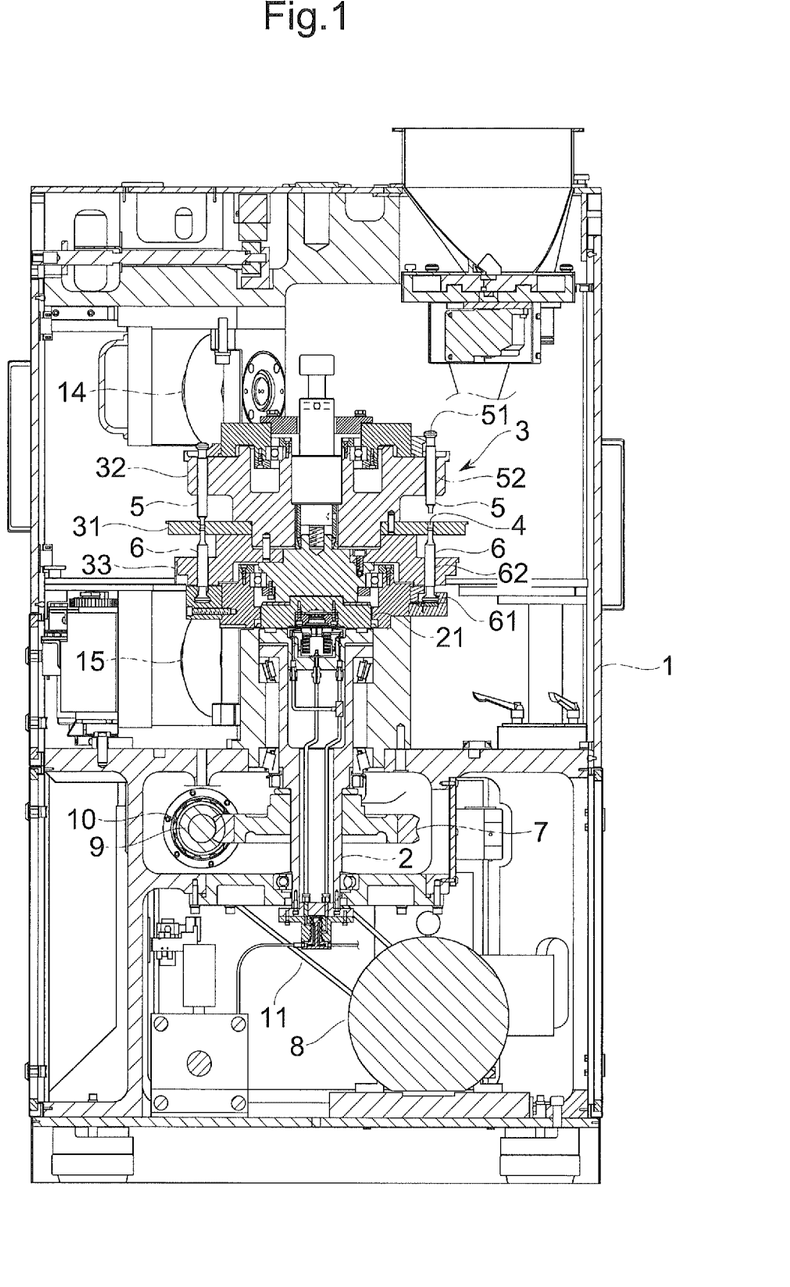
FIG. 1 is a vertical sectional view of a compression molding machine according to an embodiment of the invention.

A shown in FIG. 1, there is provided an upright shaft 2 that stands in the frame 1 of the rotary compression molding machine and functions as a rotary shaft, and a turret 3 is attached to a connection portion 21 that is located at an upper portion of the upright shaft 2.

Figure 2:
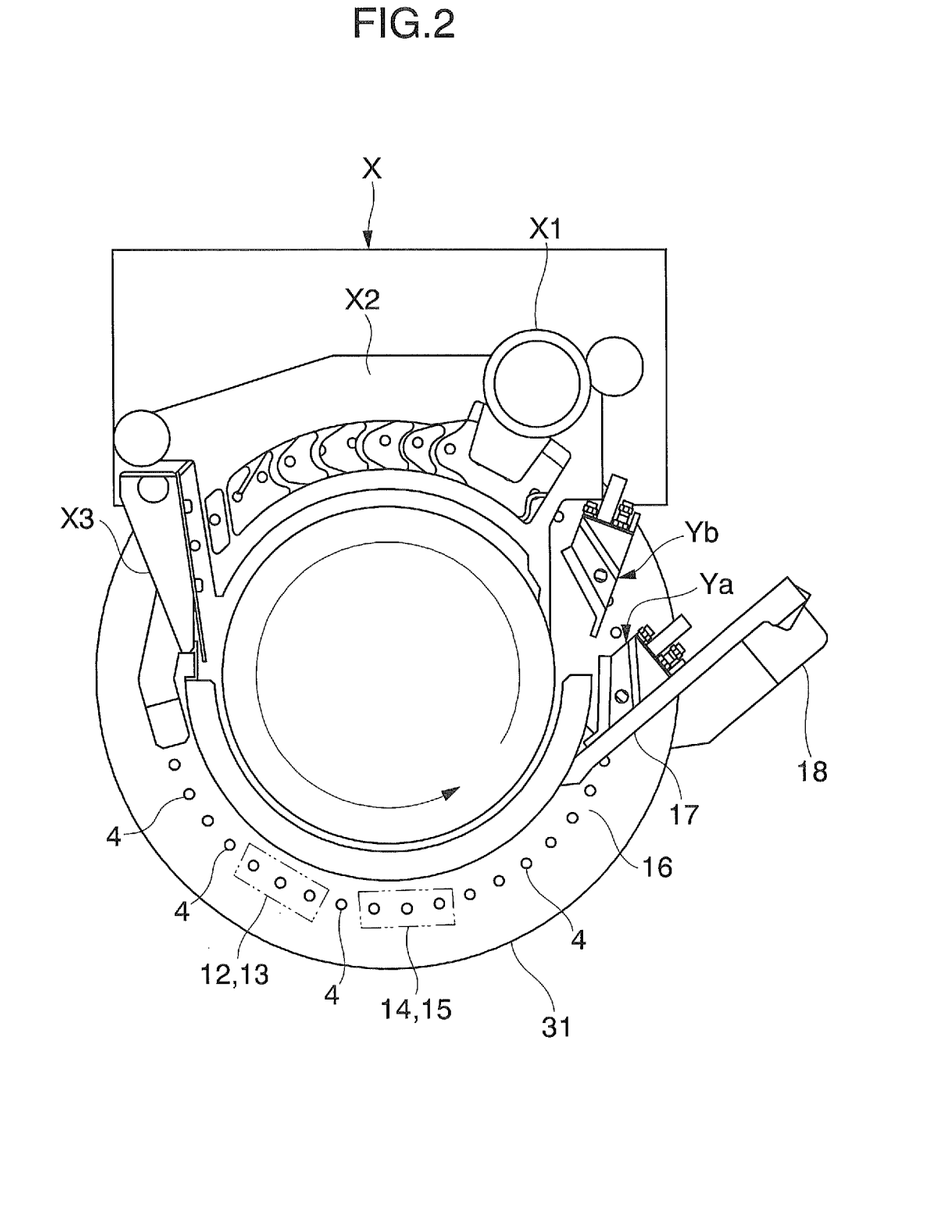
FIG. 2 is a plan view of a main portion of the compression molding machine according to the embodiment.

The turret 3 horizontally rotates about the upright shaft 2, more specifically, spins. The turret 3 is configured by the table (die disc) 31, an upper punch retaining portion 32, and a lower punch retaining portion 33. As shown in FIG. 2, the table 31 has a substantially circular disc shape, and a plurality of die bores 4 are provided in an outer peripheral portion thereof so as to be aligned in a direction of rotation and be spaced apart from each other at predetermined intervals. The die bores 4 each penetrate the table 31 in the vertical direction. The table 31 may be composed of a plurality of divided plates. Instead of the die bores 4 provided directly in the table 31, a plurality of die members may be provided separately from the table 31 so as to be detachably attached to the table 31. In this case, the die members are each provided with a die bore that penetrates in the vertical direction.

The upper punch 5 and the lower punch 6 are retained above and below corresponding one of the die bores 4, by the upper punch retaining portion 32 and the lower punch retaining portion 33, so as to be individually slidable in the die bore 4 in the vertical direction. Each upper punch 5 has a tip 53 that enters and exits the corresponding die bore 4. Each lower punch 6 has a tip 63 that is always inserted in the corresponding die bore 4. The upper punch and the lower punch 6 horizontally rotate about the upright shaft 2 together with the turret 3, more specifically, revolve.

The upright shaft 2 is provided, at the lower end, with a worm wheel 7. The worm wheel 7 meshes with a worm gear 10. The worm gear 10 is fixed to a gear shaft 9 that is driven by a motor 8. Drive power outputted from the motor 8 is transmitted to the gear shaft 9 by way of a belt 11, so as to drive to rotate the upright shaft 2 by way of the worm gear 10 and the worm wheel 7, and further to rotate the turret 3 as well as the punches 5 and 6.

Figure 3:
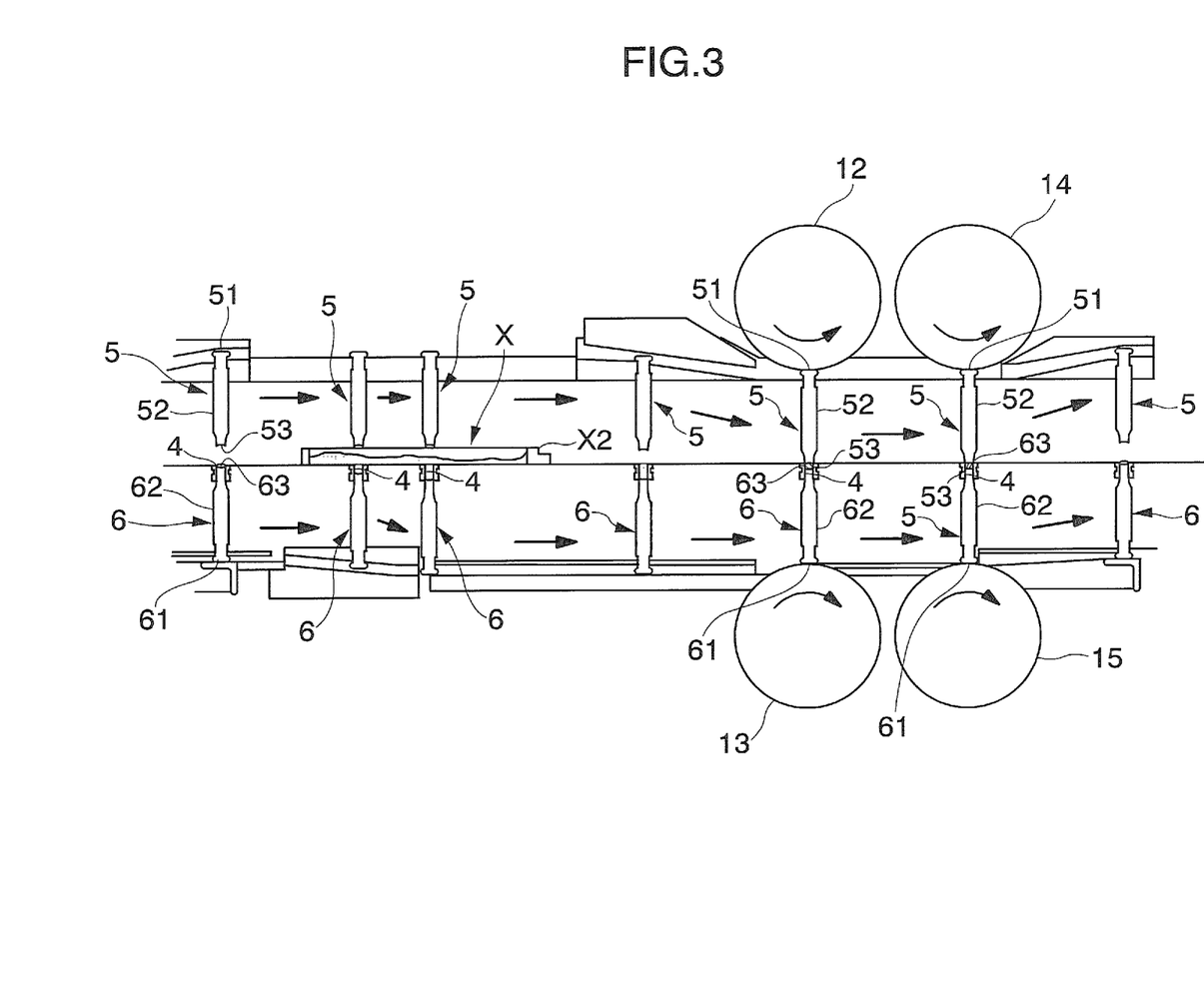
FIG. 3 is a cylindrical projection view showing the relationship between punches and rolls in the compression molding machine according to the embodiment.

A shown in FIGS. 2 and 3, a pre compression upper roll 12, a pre compression lower roll 13, a main compression upper roll 14, and a main compression lower roll 15 are provided on orbits of the punches 5 and 6 that revolve about the upright shaft 2. The pre compression upper roll 12 and the pre compression lower roll 13, as well as the main compression upper roll 14 and the main compression lower roll 15, are respectively paired in the vertical direction so as to sandwich the punches 5 and 6. The pre compression upper roll 12 and the pre compression lower roll 13, as well as the main compression upper roll 14 and the main compression lower roll 15, respectively bias the upper and lower punches 5 and 6 to bring the upper and lower punches 5 and 6 close to each other, so that the tips 53 and 63 compress from above and below the powdery material, which is filled in each of the die bores 4.

The upper punch 5 and the lower punch 6 have head portions 51 and 61 that are pressed by the rolls 12, 13, 14, and 15, and shaft portions 52 and 62 that are smaller in diameter than the head portions 51 and 61, respectively. The shaft portions 52 and 62 each have a distal end of a diameter smaller than remaining portions and substantially equal to the inner diameter of the die bore 4, so as to be inserted into the die bore 4. The punches 5 and 6 revolve to bring the rolls 12, 13, 14, and 15 close to the head portions 51 and 61 of the punches 5 and 6. The rolls 12, 13, 14, and 15 move to step onto the head portions 51 and 61 and come into contact therewith. Further, the rolls 12, 13, 14, and 15 roll over the head portions 51 and 61 and are displaced in the horizontal direction, during which pressing downward each upper punch 5 and pressing upward each lower punch 6, respectively. While the rolls 12, 13, 14, and 15 are in contact with top flat surfaces of the punches 5 and 6, the punches 5 and 6 keep applying constant pressure onto the powdery material in the corresponding die bore 4.

A molded product unloading portion 16 is provided ahead, in the directions of rotation of the turret 3 and the punches 5 and 6, of the position where the main compression upper roll 14 and the main compression lower roll 15 apply pressure. At the molded product unloading portion 16, the lower punch 6 ascends until the upper end surface of the tip 63 of the lower punch 6 reaches the height substantially same as that of the upper end of the die bore 4, in other words, the upper surface of the table 31. The lower punch 6 then pushes the molded product out of the die bore 4. The molded product unloading portion 16 is provided with a guide member 17 that guides the molded product pushed out of the die bore 4. The molded product extracted from the die bore 4 is brought into contact with the guide member 17 due to the rotation of the turret 3, and is shifted along the guide member 17 toward a molded products collecting position 18.

The filling device X fills the powdery material into the die bore 4. The filling device X has, as its elements, a powdery material supply mechanism X1, a feed shoe X2, and a level-off plate X3. The powdery material supply mechanism X1 guides the powdery material onto the revolution orbit of the die bore 4. The feed shoe X2 drops and fills the powdery material supplied by the powdery material supply mechanism X1 into the die bore 4 as the lower punch 6 moves down to a predetermined height. The level-off plate X3 levels off the powdery material that overflows the die bore 4 as the lower punch 6 moves up after the powdery material is filled by the feed shoe X2.

Figure 4:
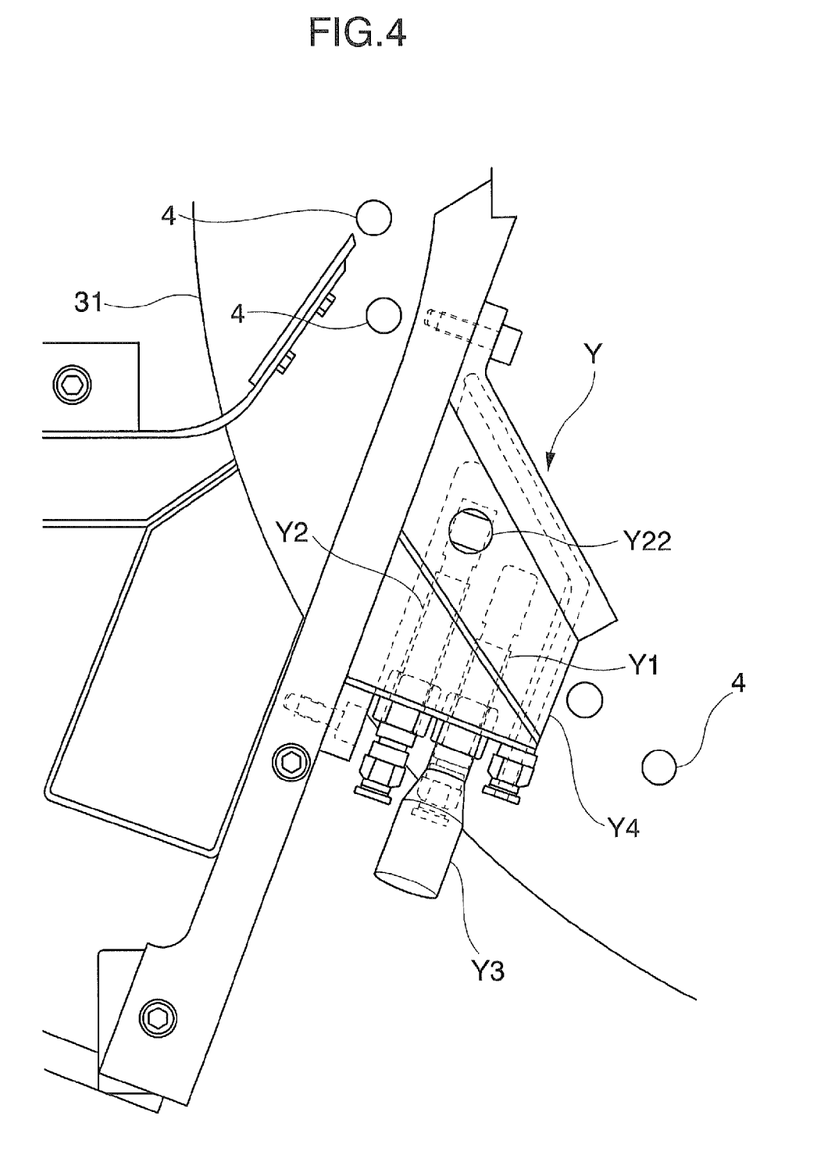
FIG. 4 is an enlarged plan view of a main portion of a spray device in the compression molding machine according to the embodiment.

A spray device Y (Ya or Yb) sprays powder propellant other than a powdery material onto an inner circumferential surface of the die bore 4, an upper end surface of the tip 63 of the lower punch 6, and a lower end surface of the tip 53 of the upper punch 5. As shown in FIG. 4, the spray device Y includes, as its elements, a downward spray nozzle Y1 for guiding propellant supplied from an external propellant supply device (not shown) and spraying the propellant toward the die bore 4 and the upper end surface of the tip 63 of the lower punch 6; an upward spray nozzle Y2 for guiding propellant supplied from the propellant supply device and spraying the propellant toward the lower end surface of the tip 53 of the upper punch 5; a purging suction duct Y3 for sucking surplus propellant or the like that does not adhere to the die bore 4 or the tips 53 and 63 of the punches 5 and 6 and discharging outside the sucked propellant or the like (the propellant may be fed back to the propellant supply device); and a case Y4 holding the downward spray nozzle Y1, the upward spray nozzle Y2, and the suction duct Y3.

Figure 5:
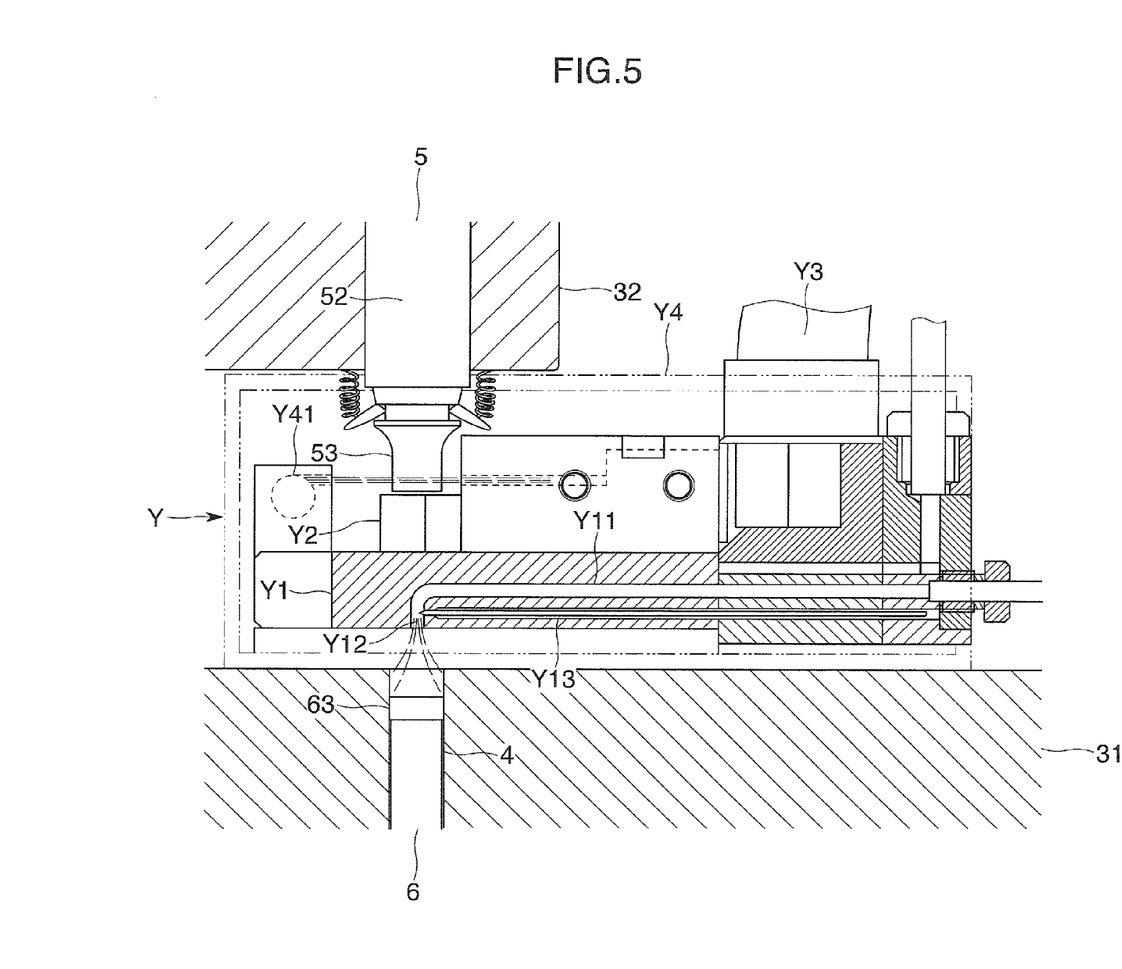
FIG. 5 is a vertical sectional view of the main portion of the spray device in the compression molding machine according to the embodiment.

As shown in FIG. 5, the downward spray nozzle Y1 has a distribution pipe Y11 formed by boring a hole in a block made of fluororesin (particularly, polytetrafluoroethylene) and extending in a substantially horizontal direction, and a spray port Y12 formed by bending downward a terminal end of the distribution pipe Y11 so as to be opened to a lower surface of the block. The distribution pipe Y11 and the spray port Y12 have inner surfaces as flat surfaces of the fluororesin, thereby smoothing distribution and spraying of propellant. The downward spray nozzle Y1 has a static electricity generation electrode Y13 buried therein. The static electricity generation electrode Y13 has a distal end in a needle or tapered shape, and protrudes in an area close to the spray port Y12. The static electricity generation electrode Y13 receives high DC voltage of about −20 kV, and forcibly electrostatically charges propellant immediately before being sprayed with an electric field concentrated at the distal end thereof.

The upward spray nozzle Y2 is structured such that the downward spray nozzle Y1 shown in FIG. 5 is placed upside down. More specifically, the upward spray nozzle Y2 has a distribution pipe formed by boring a hole in a block made of fluororesin and extending in a substantially horizontal direction, and a spray port Y22 formed by bending upward a terminal end of the distribution pipe so as to be opened to an upper surface of the block. The upward spray nozzle Y2 also has a static electricity generation electrode buried therein. The static electricity generation electrode has a distal end in a needle or tapered shape, and protrudes in an area close to the spray port Y22.

The suction duct Y3 is located in a position having a height facing a side of the tip 53 of the upper punch 5. An opening portion of the suction duct Y3 is fixed to the case Y4 and communicates with an internal space of the case Y4. The case Y4 has a box body made of fluororesin that mostly covers the downward spray nozzle Y1 and the upward spray nozzle Y2 so as to prevent random dispersion of propellant. The case Y4 is electrically insulated from the turret 3 and the spray nozzles Y1 and Y2. The case Y4 has an air curtain Y41 formed by blowing out compressed air substantially in a horizontal direction toward the opening of the suction duct Y3. The air curtain Y41 forms an air flow in the vicinity of the tip 53 of the upper punch 5, and prevents upward scatter of propellant that is sprayed from the upward spray nozzle Y2 toward the tip 53 of the upper punch 5.

The external propellant supply device is known and includes a μR feeder unit (product name of Nisshin Engineering Inc.) that extracts propellant accurately stably little by little with use of a filling roll of a thin-groove filling type and pneumatically feeds the extracted propellant by means of pressurized air.

Propellant supplied from the propellant supply device is divided into the downward spray nozzle Y1 and the upward spray nozzle Y2, flows through the distribution pipes in the nozzles Y1 and Y2, and is sprayed out of the spray ports Y12 and Y22. The propellant being sprayed is forcibly electrostatically charged. The die bore 4 and the punches 5 and 6 are grounded via ground of the turret 3. The electrostatically charged propellant strongly adheres to the inner circumferential surface of the die bore 4, the upper end surface of the tip 63 of the lower punch 6, and the lower end surface of the tip 53 of the upper punch 5, which are metal surfaces. The propellant having adhered is not separated by vibration of the punches 5 and 6 moving upward and downward or wind pressure caused by rapid rotation of the turret 3. The propellant having adhered is pressed strongly against a powdery material simultaneously when the punches 5 and 6 compress to mold the powdery material, and is transferred from the die bore 4 and the tips 53 and 63 of the punches 5 and 6 to adhere to a tablet.

As shown in FIG. 2, there are provided a plurality of spray devices Y in this embodiment. The first spray device Ya, the second spray device Yb, the filling device X, pre-compression rolls 12 and 13, main compression rolls 14 and 15, and the molded product unloading portion 16 are aligned in this order in the direction of rotation of the turret 3. The first spray device Ya sprays outer lubricant K as propellant, whereas the second spray device Yb sprays a light coloring substance T as propellant.

The outer lubricant K sprayed from the first spray device Ya prevents binding of a powdery material M adhering to the inner circumference of the die bore 4 and sticking of the powdery material M adhering to the tips 53 and 63 of the punches 5 and 6 (each of which causes a scratch, rough shaping, or a crack of a molded product). Examples of the lubricant K include metal stearate (particularly magnesium stearate) and talc. Examples of the light coloring substance T sprayed from the second spray device Yb include magnesium oxide, zinc oxide, aluminum oxide, anatase type titanium oxide, rutile type titanium dioxide, red ferric oxide, and yellow ferric oxide. Particular examples thereof include substances colored by applying ultraviolet light, such as anatase type titanium oxide, rutile type titanium dioxide, red ferric oxide, and yellow ferric oxide.

Figure 6:
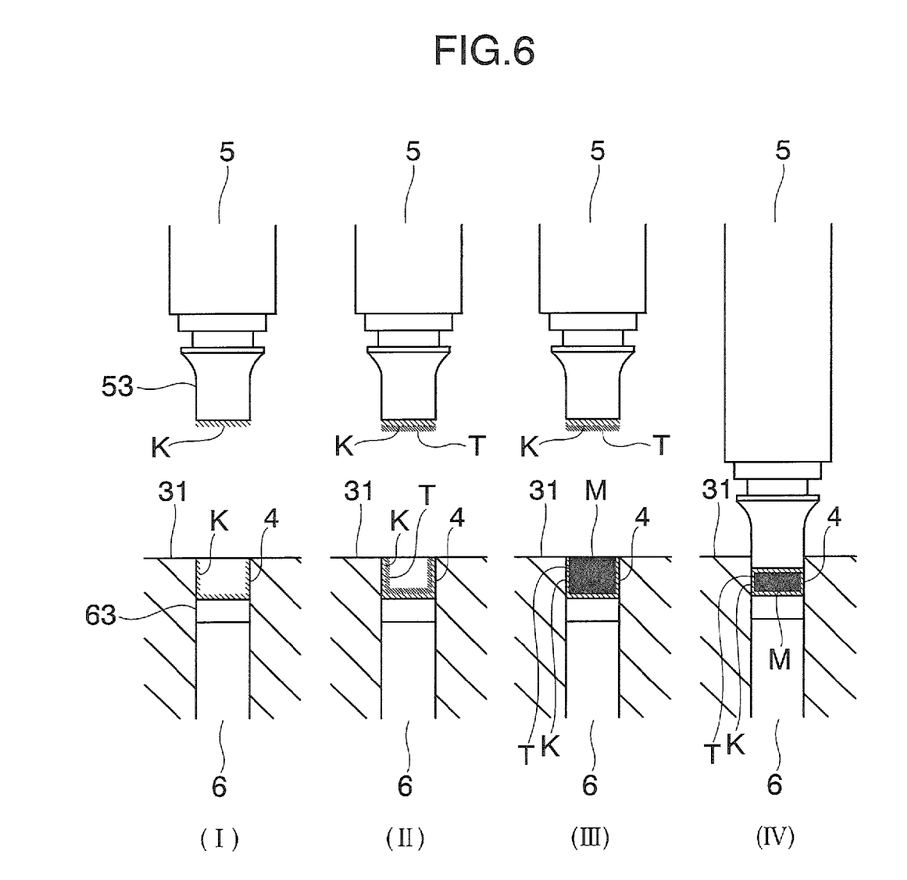

The rotary compression molding machine according to this embodiment performs the following steps of producing a molded product. Initially as shown in FIG. 6(I), the first spray device Ya sprays to apply outer lubricant K onto the inner circumferential surface of the die bore 4, the upper end surface of the tip 63 of the lower punch 6, and the lower end surface of the tip 53 of the upper punch 5. Subsequently as shown in FIG. 6(II), the second spray device Yb sprays to apply light coloring substance T onto the inner circumferential surface of the die bore 4, the upper end surface of the tip 63 of the lower punch 6, and the lower end surface of the tip 53 of the upper punch 5, so that the light coloring substance T is coated on the outer lubricant K. Then as shown in FIG. 6(III), the filling device X fills powdery material M in the die bore 4. Thereafter as shown in FIG. 6(IV), the upper punch 5 and the lower punch 6 are pressed by the pre-compression rolls 12 and 13 to pre-compress the powdery material M in the die bore 4, and are further pressed by the main compression rolls 14 and 15 to mainly compress the powdery material M in the die bore 4. A molded product obtained by compression molding can have a letter or the like on a surface thereof by the coloring step of applying light from an ultraviolet laser or the like.

Figure 7:
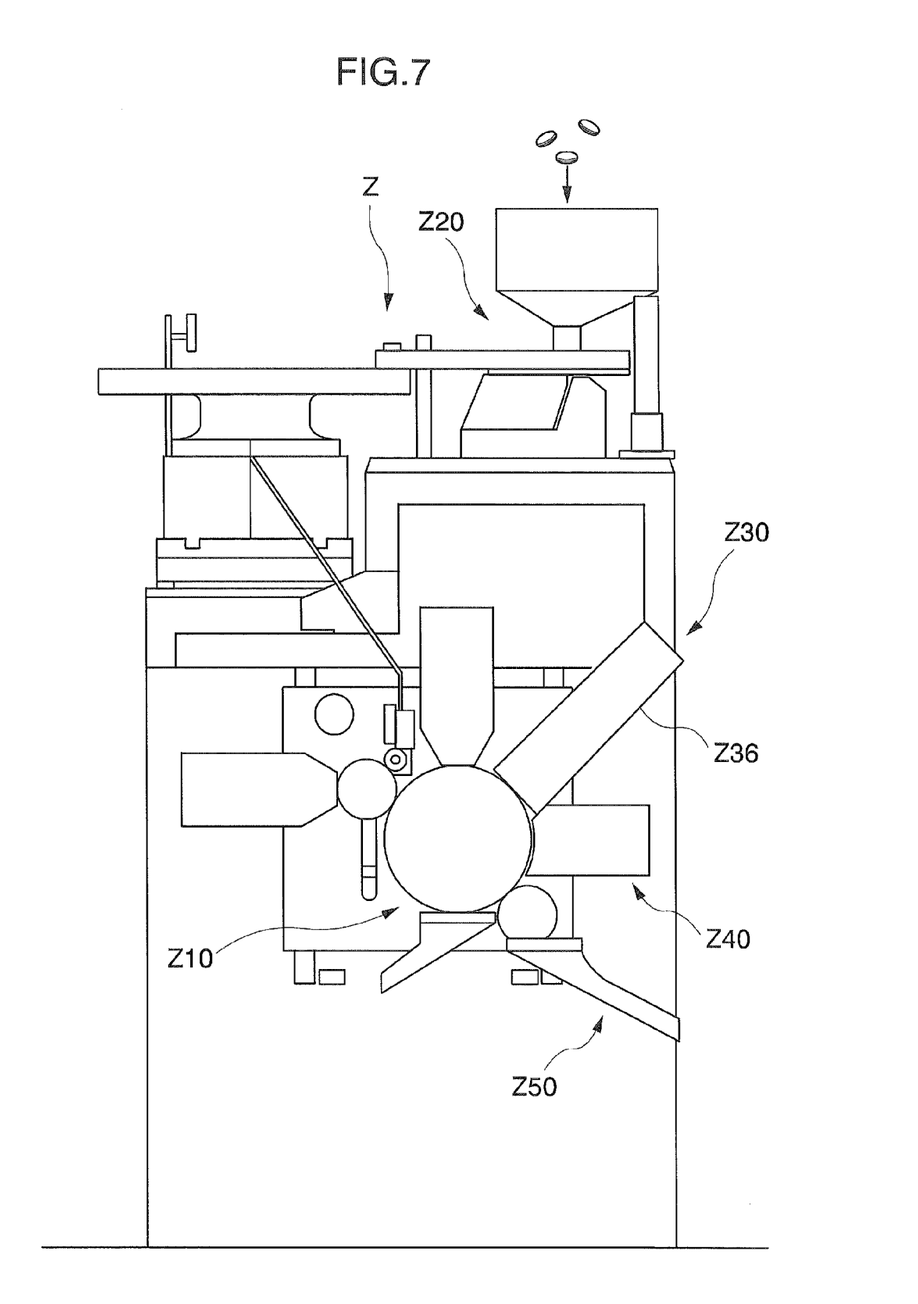
FIG. 7 is a schematic outer view of a laser marking device used in an embodiment of the invention.

A specific example of the coloring step in the invention is described below. FIG. 7 is a side view showing a schematic configuration of a laser marking device Z used in the coloring step of the invention. The laser marking device Z marks on a surface of a molded product such as a tablet.

As shown in FIG. 7, the laser marking device Z includes a conveyer drum Z10, a feeder Z20, a laser light scanner Z30, a marking checker Z40, and a discharger Z50. The conveyer drum Z10 retains a molded product on an outer circumferential surface thereof and rotates to convey the molded product. The feeder Z20 feeds a molded product to the conveyer drum Z10. The laser light scanner Z30 applies laser light to the molded product conveyed by the conveyer drum Z10 to mark on the molded product. The marking checker Z40 checks the state of marking on the molded product. The discharger Z50 discharges a solid material having been checked. Mainly described in this embodiment is a configuration of the laser light scanner Z30.

Figure 8:
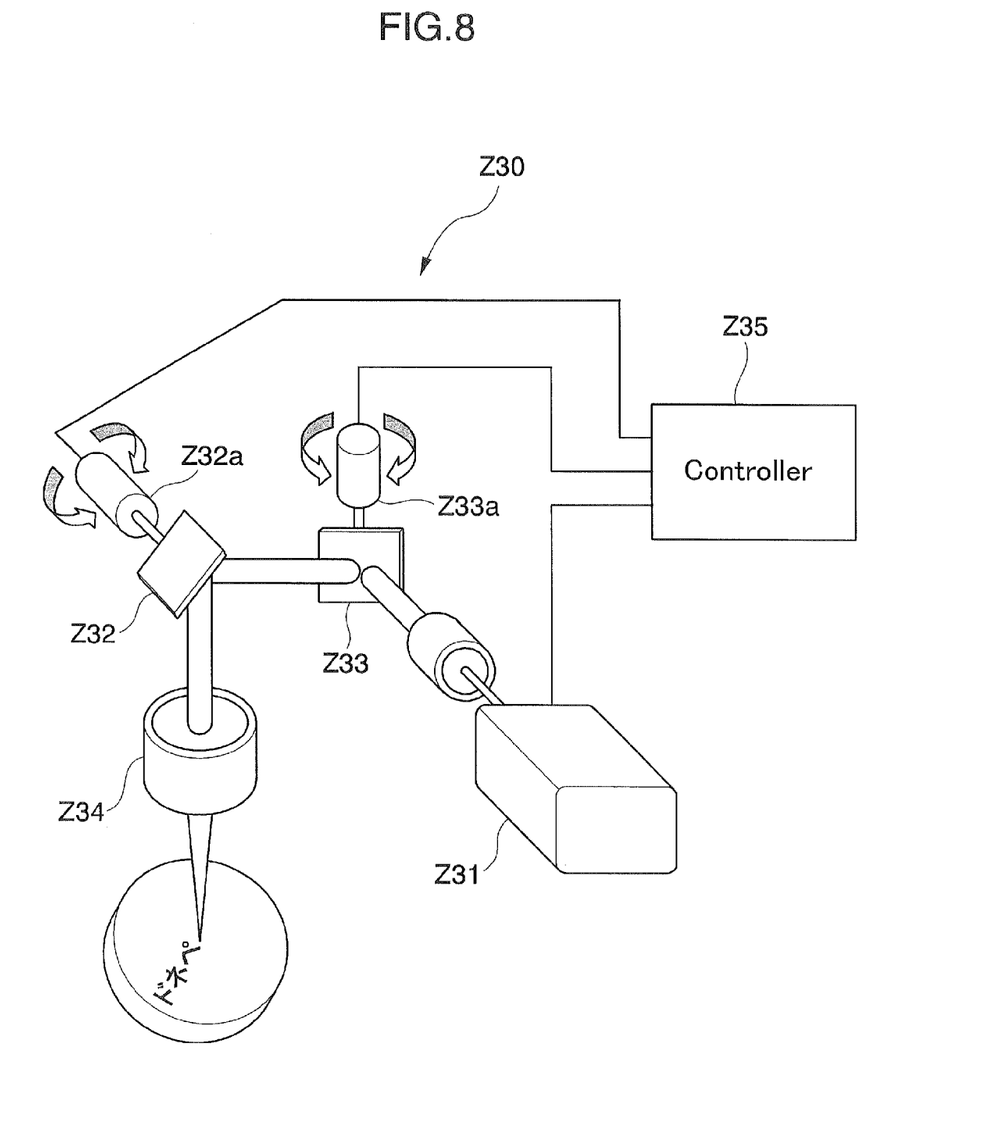
FIG. 8 is a schematic explanatory view of a main portion of the laser marking device.

As shown in FIG. 7, the laser light scanner Z30 is located near the conveyer drum Z10 and downstream of the feeder Z20 in the direction of conveying a molded product. As schematically shown in FIG. 8, the laser light scanner Z30 includes a laser light source Z31, a pair of galvanometer mirrors Z32 and Z33, a convergence lens Z34, and a controller Z35.

The laser light source Z31 emits laser light to form a marking pattern on a molded product. The laser according to this embodiment has output of 0.1 to 10 W and a wavelength of 200 to 1100 nm. In a case of marking by burning an ingredient on the surface of a molded product, the laser preferably has a wavelength of 1060 to 1064 nm. On the other hand, in a case of using the light coloring substance T as in this embodiment, the laser preferably has a wavelength of 351 to 355 nm or 263 to 266 nm.

The paired galvanometer mirrors Z32 and Z33 have reflection angles that can be changed by drives Z32a and Z33a such as servomotors, respectively. The galvanometer mirror Z32 can change the reflection angle in an X direction, whereas the galvanometer mirror Z33 can change the reflection angle in a Y direction. Laser light emitted from the laser light source Z31 can thus be applied to the conveyer drum Z10 in circumferential and axial directions thereof in a marking area on the conveyer drum Z10.

The convergence lens Z34 can be an f-θ lens, and converges laser light reflected by the pair of galvanometer mirrors Z32 and Z33 to a surface of a molded product. The convergence lens Z34 is supported so as to be movable in the vertical direction, so as to appropriately adjust a focal position of laser light.

The controller Z35 stores in a memory (not shown) marking information on marking patterns to be formed on a molded product, such as letters, symbols, and graphics designed with CAD or the like. The controller Z35 captures a rotational position of the conveyer drum Z10 by detection of a rotary encoder as well as controls emission from the laser light source Z31 and activation of the drives Z32a and Z33a in accordance with marking information, so as to mark on each molded product.

Erroneous filling or detachment of a molded product in or from the conveyer drum Z10 can be determined between the feeder Z20 and the laser light scanner Z30, by an outer appearance checker Z60 for detecting a filling state of the conveyer drum Z10. The controller Z35 controls emission of the laser light source Z31 so as not to perform marking if the outer appearance checker Z60 does not detect any molded product.

The laser light scanner Z30 is covered with a cylindrical protective cover Z36. The protective cover Z36 has a side surface connected with a suction unit (not shown) for sucking dust generated during marking. The laser light scanner Z30 further includes a neutralizer (not shown) for removing electricity of a solid material having been marked.

As described above, the method of producing a solid material according to this embodiment can be easily embodied by including the coloring step of applying light on a surface of a molded product that is obtained by compressing and molding a powdery material such as medicine with use of the compression molding machine.

Specific configurations of other respective portions are not limited to those in the embodiment either and the invention may be modified in various ways within a range not departing from the purposes thereof.

For example, the above embodiment refers to the aspect of obtaining a molded product by applying a light coloring substance on an entire surface of a compressed and molded powdery material. Alternatively, a molded product can be obtained by applying a light coloring substance on only one of the upper and lower punches so as to apply the light coloring substance on one of upper and lower surfaces of the molded product. Furthermore, the above embodiment refers to a solid material that has printing on only one of the surfaces of the molded product. Alternatively, it is possible to produce a solid material that has printing on both of the upper and lower surfaces or on a side surface of the molded product. Moreover, specific aspects of the laser marking device and the powdery material to be compressed and molded are not limited to those of the above embodiment, but may be modified in various ways inclusive of conventional aspects.

Second Embodiment

A compression molding machine according to the second embodiment sprays a mixture TK of outer lubricant K and a light coloring substance T. Described mainly below are differences from the first embodiment. Configurations in common with the first embodiment will not be described repeatedly.

Figure 9:
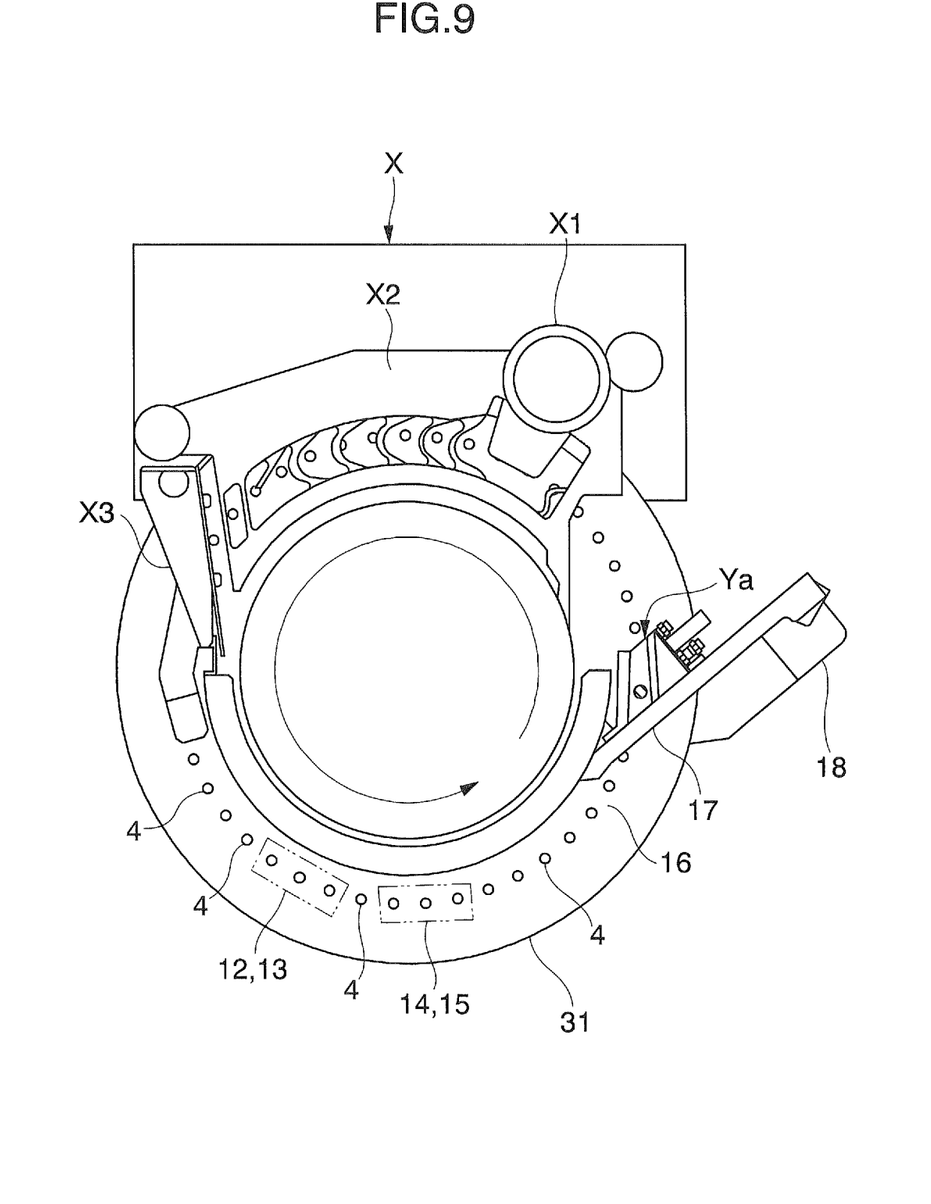
FIG. 9 is a plan view of a main portion of a compression molding machine according to an embodiment of the invention.

The rotary compression molding machine according to this embodiment performs the following steps of producing a molded product. As shown in FIG. 9, the first spray device Ya sprays to apply a mixture of the outer lubricant K and the light coloring substance T onto the inner circumferential surface of the die bore 4, the upper end surface of the tip 63 of the lower punch 6, and the lower end surface of the tip 53 of the upper punch 5. The filling device X then fills the powdery material M in the die bore 4. Thereafter, the upper punch 5 and the lower punch 6 are pressed by the pre-compression rolls 12 and 13 to pre-compress the powdery material M in the die bore 4. The upper punch 5 and the lower punch 6 are further pressed by the main compression rolls 14 and 15 to mainly compress the powdery material M in the die bore 4. A molded product obtained by compression molding can have a letter or the like on a surface thereof by the coloring step of applying light from an ultraviolet laser or the like.

Mixing the light coloring substance T and the outer lubricant K effectively enables the light coloring substance T, which is highly aggregable, to be sprayed without stuck before the spraying step. In addition, there is no need to separately spray the outer lubricant K. The light coloring substance T is applied on the surface of the molded product and is also improved in coloring property because there is no need to separately spray the outer lubricant K.

Specific configurations of other respective portions are not limited to those in the embodiment either and the invention may be modified in various ways within a range not departing from the purposes thereof.

Described below are specific examples of this embodiment.

The second embodiment is described below by referring to reference examples and examples, although the invention should not be limited by these reference examples and examples.

Reference Example 1

Production of Powdery Material

First, 792.5 g of pregelatinized starch (PCS/Asahi Kasei Chemicals) was fed in a fluidized bed granulating-dry coating machine (MP-01SPC/Powrex), and a solution prepared by preliminarily dissolving and dispersing 250 g of donepezil hydrochloride (TEVA) and 7.5 g of a polyvinyl alcohol-acrylic acid-methyl methacrylate copolymer (POVA-COAT/Daido Chemical Corporation) in 750 g of purified water was sprayed to the pregelatinized starch thus fed so as to granulate by layering.

The agglomerated material thus obtained was then sprayed and coated with a solution prepared by preliminarily dissolving and dispersing 20 g of a polyvinyl alcohol copolymer and talc (Crown talc/Matsumura Industry) in 1300 g of purified water and was dried. The agglomerated material thus dried was further coated with a solution prepared by dissolving and dispersing 1500 g of methacrylic acid copolymer LD (Eudragit L30D55/Evonik Degussa Japan), 125 g of D-mannitol (Mannit P/Mitsubishi Shoji Foodtech), 125 g of talc, and triethyl citrate (Citroflex 2SC-60/MORIMURA BROS.) in 1875 g of purified water and was dried to obtain coated granules.

These coated granules, 3890.5 g of D-mannitol, crystalline cellulose (CEOLUS KG-802/Asahi Kasei Chemicals), and 1000 g of low substituted hydroxy-propylcellulose (NBD-022/Shin-Etsu Chemical) were fed in a fluidized bed granulating-dry coating machine (FD-GPCG-5SPC/Powrex), were granulated while spraying a solution prepared by dissolving 90 g of hydroxypropyl cellulose (HPC-L/Nippon Soda) in 2910 g of purified water, and were dried to obtain agglomerated granules.

These agglomerated granules, 150 g of crystalline cellulose, 12 g of l-menthol (K. Kobayashi), 150 g of aspartame (Ajinomoto), 7.5 g of flavoring agent (Dry coat strawberry/TAKATA KORYO), and 100 g of Magnesium Stearate (magnesium stearate) (TAIHEI CHEMICAL INDUSTRIAL) were fed in a tumbler mixer (TM-15S/Showa Giken) and were mixed together to obtain a powdery material for orally disintegrating tablets of donepezil hydrochloride.

In each of Examples 1 to 8 to be described below, 200 g of this powdery material was compressed and molded with use of a rotary compression molding machine (AQUARIUS 3/Kikusui Seisakusho) equipped with an external lubricating device (ELS-P1/Kikusui Seisakusho). A mixture of a light coloring substance T (titanium oxide or red ferric oxide) and an outer lubricant K was sprayed to a mold tool with use of the external lubricating device to produce orally disintegrating tablets (8 mm in diameter, 3.3 mm in thickness, and 190 mg in mass for one tablet), to measure the amount of titanium oxide or red ferric oxide deposited on the orally disintegrating tablets.

Figure 10:
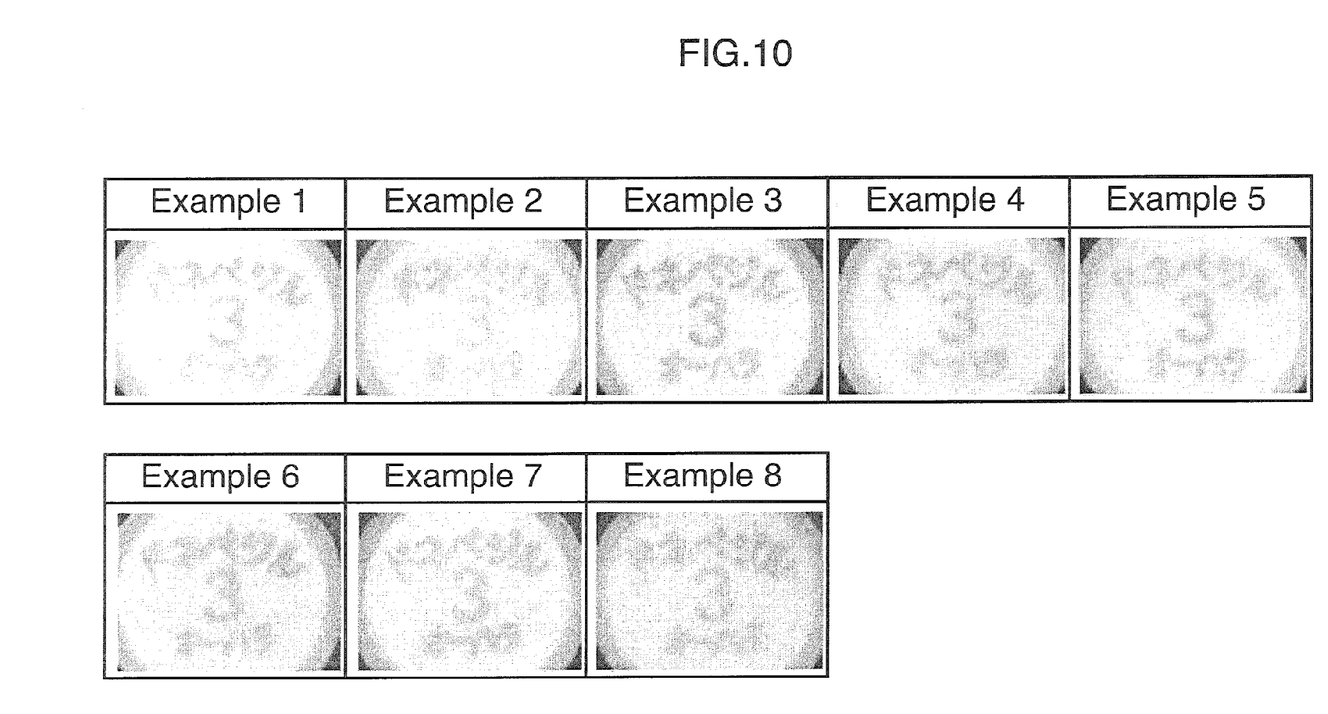
FIG. 10 includes pictures substituting for drawings, showing orally disintegrating tablets obtained in Examples 1 to 8, each having letters displayed by irradiation with ultraviolet laser light.

The orally disintegrating tablets produced in Examples 1 to 8 were irradiated with ultraviolet laser light to check the states of letters or the like and disintegrability (FIG. 10).

Example 1

A mixture preliminarily obtained by uniformly mixing 500 g of titanium oxide and 500 g of magnesium stearate was sprayed to the tip surfaces of the upper punches 5 and the lower punches 6 and into the die bores 4 at a spray flow rate of 28 g per hour with use of the external lubricating device and was tabletted at a speed of 30 rotations per minute to obtain orally disintegrating tablets. The amount of the titanium oxide deposited on the surfaces of the tablets was 0.86 mg/cm$^2$.

Example 2

A mixture preliminarily obtained by uniformly mixing 300 g of titanium oxide and 700 g of magnesium stearate was sprayed to the tip surfaces of the upper punches 5 and the lower punches 6 and into the die bores 4 at a spray flow rate of 78 g per hour with use of the external lubricating device and was tabletted at a speed of 30 rotations per minute to obtain orally disintegrating tablets. The amount of the titanium oxide deposited on the surfaces of the tablets was 0.46 mg/cm$^2$.

Example 3

A mixture preliminarily obtained by uniformly mixing 200 g of red ferric oxide and 800 g of magnesium stearate was sprayed to the tip surfaces of the upper punches 5 and the lower punches 6 and into the die bores 4 at a spray flow rate of 76 g per hour with use of the external lubricating device and was tabletted at a speed of 30 rotations per minute to obtain orally disintegrating tablets. The amount of the red ferric oxide deposited on the surfaces of the tablets was 0.05 mg/cm$^2$.

Example 4

A mixture preliminarily obtained by uniformly mixing 100 g of yellow ferric oxide and 900 g of magnesium stearate was sprayed to the tip surfaces of the upper punches 5 and the lower punches 6 and into the die bores 4 at a spray flow rate of 72 g per hour with use of the external lubricating device and was tabletted at a speed of 30 rotations per minute to obtain orally disintegrating tablets. The amount of the yellow ferric oxide deposited on the surfaces of the tablets was 0.06 mg/cm$^2$.

Example 5

A mixture preliminarily obtained by uniformly mixing 50 g of titanium oxide and 950 g of magnesium stearate was sprayed to the tip surfaces of the upper punches 5 and the lower punches 6 and into the die bores 4 at a spray flow rate of 72 g per hour with use of the external lubricating device and was tabletted at a speed of 30 rotations per minute to obtain orally disintegrating tablets. The amount of the titanium oxide deposited on the surfaces of the tablets was 0.16 mg/cm$^2$.

Example 6

A mixture preliminarily obtained by uniformly mixing 200 g of titanium oxide, 700 g of stearic acid, and 100 g of magnesium stearate was sprayed to the tip surfaces of the upper punches 5 and the lower punches 6 and into the die bores 4 at a spray flow rate of 112 g per hour with use of the external lubricating device and was tabletted at a speed of 30 rotations per minute to obtain orally disintegrating tablets. The amount of titanium oxide deposited on the surfaces of the tablets was 0.36 mg/cm$^2$.

Example 7

A mixture preliminarily obtained by uniformly mixing 200 g of titanium oxide, 700 g of hydroxypropylcellulose, and 100 g of magnesium stearate was sprayed to the tip surfaces of the upper punches 5 and the lower punches 6 and into the die bores 4 at a spray flow rate of 86 g per hour with use of the external lubricating device and was tabletted at a speed of 30 rotations per minute to obtain orally disintegrating tablets. The amount of titanium oxide deposited on the surfaces of the tablets was 0.21 mg/cm$^2$.

Example 8

A mixture preliminarily obtained by uniformly mixing 200 g of titanium oxide, 700 g of corn starch, and 100 g of magnesium stearate was sprayed to the tip surfaces of the upper punches 5 and the lower punches 6 and into the die bores 4 at a spray flow rate of 110 g per hour with use of the external lubricating device and was tabletted at a speed of 30 rotations per minute to obtain orally disintegrating tablets. The amount of titanium oxide deposited on the surfaces of the tablets was 0.19 mg/cm$^2$.

Table 1 collectively indicates details of Examples 1 to 8.

TABLE 1

| | Sample | | | Amount deposited |
|---|---|---|---|---|
| Example 1 | Titanium oxide 500 g | Magnesium stearate 500 g | | Titanium oxide 0.86 mg |
| Example 2 | Titanium oxide 300 g | Magnesium stearate 700 g | | Titanium oxide 0.46 mg |
| Example 3 | Red ferric oxide 200 g | Magnesium stearate 800 g | | Red ferric oxide 0.05 mg |
| Example 4 | Red ferric oxide 100 g | Magnesium stearate 900 g | | Red ferric oxide 0.06 mg |
| Example 5 | Titanium oxide 50 g | Magnesium stearate 950 g | | Titanium oxide 0.16 mg |
| Example 6 | Titanium oxide 200 g | Stearic acid 700 g | Magnesium stearate 100 g | Titanium oxide 0.36 mg |
| Example 7 | Titanium oxide 200 g | Hydroxypropyl-cellulose 700 g | Magnesium stearate 100 g | Titanium oxide 0.21 mg |
| Example 8 | Titanium oxide 200 g | Corn starch 700 g | Magnesium stearate 100 g | Titanium oxide 0.19 mg |

These orally disintegrating tablets produced in Examples 1 to 8 were irradiated with laser light with use of a ultraviolet laser marking device (LIS-250/Qualicaps) at PE=38% and 30000 Hz so as to provide letters (FIG. 10).

The letters colored and provided by irradiating with ultraviolet laser light on the orally disintegrating tablets produced in Examples 1 to 8 have clear distinguishability as shown in FIG. 10.

Table 2 indicates results of hardness and an orally disintegrating period of an orally disintegrating tablet according to a comparative example to be described below and the orally disintegrating tablets according to Examples 1 to 8.

As indicated in Table 2, the orally disintegrating tablets according to Examples 1 to 8 exhibited the results similar to the orally disintegrating tablet according to the comparative example.

The invention accordingly achieves provision of a letter or the like with use of ultraviolet laser light, reduction of a placement space, production steps, a production period, and a light coloring substance, without affecting disintegrability of an orally disintegrating tablet.

Comparative Example

The powdery material obtained in Reference Example 1 was compressed and molded with use of the rotary compression molding machine equipped with the external lubricating device while spraying an outer lubricant K to the tip surfaces of the upper punches 5 and the lower punches 6 and into the die bores 4 with use of the external lubricating device, to obtain orally disintegrating tablets (8 mm in diameter, 3.3 mm in thickness, and 190 mg in mass for one tablet).

TABLE 2

| Sample | Hardness of tablets (N) | Orally disintegrating period (second) |
|---|---|---|
| Example 1 | 35 | 42 |
| Example 2 | 32 | 44 |
| Example 3 | 33 | 45 |
| Example 4 | 32 | 43 |
| Example 5 | 36 | 41 |
| Example 6 | 35 | 40 |
| Example 7 | 33 | 52 |
| Example 8 | 34 | 43 |
| Comparative Example | 35 | 44 |

What is claimed is:

1. A method of producing a solid material with use of a compression molding machine including an upper punch, a lower punch, and a die bore formed in a table, the method comprising:
   applying a light coloring substance to at least one of an inner surface of the die bore, an upper end surface of the lower punch, and a lower end surface of the upper punch;
   filling a powdery material in the die bore;
   compression molding the powdery material filled in the die bore with use of the upper punch and the lower punch; and
   irradiating with light a molded product obtained by the compression molding to color the molded product,
   wherein the applying further includes spraying a mixture of outer lubricant and the light coloring substance on at least one of the inner surface of the die bore, the upper end surface of the lower punch, and the lower end surface of the upper punch in order to apply the light coloring substance on the surface of the molded product.

2. The method of producing a solid material according to claim 1, further comprising spraying outer lubricant to the inner surface of the die bore, the upper end surface of the lower punch, and the lower end surface of the upper punch.

3. A method of producing a solid material with use of a compression molding machine including an upper punch, a lower punch, and a die bore formed in a table, the method comprising:
   spraying a light coloring substance and outer lubricant to an inner surface of the die bore, an upper end surface of the lower punch, and a lower end surface of the upper punch;
   compression molding a powdery material filled in the die bore with use of the upper punch and the lower punch; and
   irradiating with light a molded product obtained by the compression molding to color the molded product,
   wherein the spraying further includes spraying a mixture of outer lubricant and the light coloring substance on at least one of the inner surface of the die bore, the upper end surface of the lower punch, and the lower end surface of the upper punch in order to apply the light coloring substance on the surface of the molded product.

4. The method of producing a solid material according to claim 1, wherein the light comprises ultraviolet laser light.

5. The method of producing a solid material according to claim 1, wherein the light coloring substance includes at least one of titanium oxide, red ferric oxide, and yellow ferric oxide.

6. The method of producing a solid material according to claim 1, wherein the solid material comprises an orally disintegrating tablet.

7. The method of producing a solid material according to claim 4, wherein the light coloring substance includes at least one of titanium oxide, red ferric oxide, and yellow ferric oxide.

8. The method of producing a solid material according to claim 2, wherein the light comprises ultraviolet laser light.

9. The method of producing a solid material according to claim 8, wherein the light coloring substance includes at least one of titanium oxide, red ferric oxide, and yellow ferric oxide.

10. The method of producing a solid material according to claim 9, wherein the solid material comprises an orally disintegrating tablet.

11. The method of producing a solid material according to claim 2, wherein the light coloring substance includes at least one of titanium oxide, red ferric oxide, and yellow ferric oxide.

12. The method of producing a solid material according to claim 11, wherein the solid material comprises an orally disintegrating tablet.

13. The method of producing a solid material according to claim 2, wherein the solid material comprises an orally disintegrating tablet.

14. The method of producing a solid material according to claim 3, wherein the light comprises ultraviolet laser light.

15. The method of producing a solid material according to claim 14, wherein the light coloring substance includes at least one of titanium oxide, red ferric oxide, and yellow ferric oxide.

16. The method of producing a solid material according to claim 15, wherein the solid material comprises an orally disintegrating tablet.

17. The method of producing a solid material according to claim 3, wherein the light coloring substance includes at least one of titanium oxide, red ferric oxide, and yellow ferric oxide.

18. The method of producing a solid material according to claim 17, wherein the solid material comprises an orally disintegrating tablet.

19. The method of producing a solid material according to claim 3, wherein the solid material comprises an orally disintegrating tablet.

* * * * *